United States Patent

Sierra

[11] Patent Number: 5,336,166
[45] Date of Patent: Aug. 9, 1994

[54] THREE STAGE IMPLANTABLE VALVE

[75] Inventor: Rolando Sierra, Grasse, France

[73] Assignee: Cordis Corporation, Miami Lakes, Fla.

[21] Appl. No.: 991,982

[22] Filed: Dec. 17, 1992

[51] Int. Cl.⁵ .............................................. A61M 27/00
[52] U.S. Cl. ........................................ 604/9; 604/247; 137/508
[58] Field of Search ...................... 137/504, 512.1, 539; 604/8, 9, 10, 247

[56] References Cited

U.S. PATENT DOCUMENTS

| | | |
|---|---|---|
| 3,886,948 | 6/1975 | Hakim . |
| 3,889,687 | 6/1975 | Harris et al. . |
| 3,924,635 | 12/1975 | Hakim . |
| 4,106,510 | 8/1978 | Hakim et al. . |
| 4,332,255 | 6/1982 | Hakim et al. . |
| 4,387,715 | 6/1983 | Hakim et al. . |
| 4,551,128 | 11/1985 | Hakim et al. . |
| 4,557,721 | 12/1985 | Hooven ............................... 604/247 |
| 4,595,390 | 6/1986 | Hakim et al. . |
| 4,621,654 | 11/1986 | Holter . |
| 4,627,832 | 12/1986 | Hooven et al. . |
| 4,675,003 | 6/2987 | Hooven . |
| 4,681,559 | 7/1987 | Hooven . |
| 4,714,458 | 12/1987 | Hooven . |
| 4,714,459 | 12/1987 | Hooven . |
| 4,729,762 | 3/1988 | Documenis . |
| 4,741,730 | 5/1988 | Dormandy, Jr. et al. . |
| 4,769,002 | 9/1988 | Hooven . |
| 4,776,838 | 10/1988 | Sainte-Rose et al. . |
| 4,776,839 | 10/1988 | Documenis . |
| 4,781,672 | 11/1988 | Hooven . |

Primary Examiner—C. Fred Rosenbaum
Assistant Examiner—N. Kent Gring
Attorney, Agent, or Firm—Lockwood, Alex, FitzGibbon & Cummings

[57] ABSTRACT

An implantable drainage device for the treatment of hydrocephalus is described. The device operates like a combination of three valves including a first pressure regulation valve in series with an assembly having a flow regulation valve in parallel with a second pressure regulation valve. The device allows cerebrospinal fluid communication between a source location in the brain and a drainage location when the pressure differential therebetween exceeds a first predetermined threshold. Above the first predetermined threshold, the device opens to allow a flow of cerebrospinal fluid therethrough, maintaining a substantially constant pressure differential across the device. When the pressure differential is between the first predetermined threshold and a second, higher, predetermined threshold a substantially constant flow rate is maintained. When the pressure differential exceeds the second predetermined threshold, the device allows a fluid flow rate sufficient to maintain a second predetermined pressure differential across the valve.

15 Claims, 2 Drawing Sheets

THREE STAGE IMPLANTABLE VALVE

BACKGROUND AND BRIEF DESCRIPTION OF THE INVENTION

The present invention relates to an implantable drainage device for the treatment of hydrocephalus. More specifically, the invention relates to an implantable three stage valve providing constant pressure or constant flow characteristics depending on the fluid pressure differential applied across the valve.

Hydrocephalus is a condition rendering the body unable to relieve itself of excess cerebrospinal fluid (CSF) collected in the ventricles of the brain. Excess CSF within the ventricular spaces results in an increase in both epidural and intradural pressures, causing a number of adverse physiological effects including compression of brain tissue, impairment of blood flow in the brain tissue and impairment of the brain's normal metabolism. The treatment of a hydrocephalic condition typically requires relieving the abnormally high intracranial pressure. Various types of valves are available to control the drainage of an excess of CSF from within the ventricles of the brain. Such valves typically drain the excess CSF to a suitable area in the body such as the peritoneal cavity, for example.

Simple pressure regulator valves or check valves are known, and typically are constructed to open and allow the drainage of fluid when the differential pressure between upstream and downstream chamber reaches a certain threshold, preventing the differential pressure from exceeding the threshold. Such simple valves do not compensate for normal differences in the differential pressure between CSF ventricular pressure and pressure in the discharge line, creating the possibility that a valve might open in response to such normal variations and possibly resulting in hyperdrainage of the ventricular spaces. For example, when a patient stands after lying in a recumbent position, the differential pressure will normally increase by reason of the resulting increased height of the fluid column between the patient's head and the selected drainage location within the abdomen, for example. While an increase in differential pressure under those conditions is normal, a check valve might respond by opening and thereby allowing undesired hyperdrainage of the ventricular spaces which, in turn, may result in a potentially serious brain hematoma.

Other types of valves, such as three stage valves, are available in which a flexible diaphragm is mounted within a housing to separate upstream and downstream chambers, and allowing fluid to flow between the chambers through a flow orifice within the diaphragm. In these types of valves, the diaphragm is subjected to the differential pressure between the upstream and downstream chambers and flexes in response to changes in pressure while the orifice interacts with a machined rod passing therethrough. Such a valve is described in U.S. Pat. No. 4,776,839 and No. 4,781,672, for example. When the diaphragm is deformed in response to increasing pressure differentials, the rod increasingly restricts the flow of fluid through the orifice, thereby regulating CSF flow over a range of pressures.

Such types of valves function as flow regulators, operating over a pressure range in which the flow of CSF remains substantially constant. These three stage valves are usually adjustable so that a lower pressure threshold or popping pressure can be preset by providing an adjustable seat against which the rim of the orifice will bear as long as the differential pressure is less than a certain threshold value. Additionally, the maximum tolerable differential pressure within such valves has a predetermined value which is met when the diaphragm experiences its maximum deformation, leaving the entire surface area of the orifice available for the flow of fluid therethrough. While performing satisfactorily, prior art three stage values have required the use of a certain machined parts such as the aforementioned stem or rod to regulate CSF flow. These parts are difficult to manufacture and, once installed in a valve, may also require complex adjustment.

The present invention overcomes these drawbacks by providing a three stage CSF valve having the desired differential pressure/flow characteristics as prior art three stage valves but which is easier and more economical to manufacture and which can be supplied in any of several embodiments. To this end, the invention provides an implantable drainage device for the treatment of hydrocephalus. The invention is embodied in a device which essentially combines three separate valves with distinct functions, the combination of which makes it possible to obtain the desired functions of a three stage valve.

More specifically, the drainage device of the invention combines at least two pressure regulation valves and a flow regulation valve. The first pressure regulation valve of the device is preset to open at a predetermined first or threshold pressure. A flow regulation valve is positioned in series with the first pressure regulation valve to regulate the CSF flow through the device, maintaining a constant flow rate over a range of differential pressures, up to a predetermined cut-off pressure. At the cut-off pressure, a second pressure regulation valve, in parallel with the flow regulation valve, opens to allow drainage at increased flow rates.

By separating the three pressure/flow functions through a combination of three different valves, the manufacture and adjustment of the drainage device of the invention is greatly simplified. Preferably, the first pressure regulation valve will be in series with an assembly of the other two valves which are arranged, most preferably, with the flow regulation valve in parallel with the second pressure regulation valve. Since the closing threshold pressure, or blow-out pressure, must be at least equal to the opening differential pressure for the second pressure regulation valve, it is preferable to provide the flow regulation valve in parallel with the second pressure regulation valve alone. Alternatively, the second pressure regulation valve can be arranged in parallel with an assembly of the other valves wherein the first pressure regulation valve is in series with the flow regulation valve.

In one embodiment of the invention, the flow regulation valve is provided with a flexible diaphragm, mounted within a single biocompatible housing and defining an upstream chamber and a downstream chamber therein. The diaphragm is provided with a central fluid flow orifice therethrough for CSF communication between the upstream and downstream chambers. The orifice is defined by upstream and downstream annular seals surrounding the orifice on the upstream and downstream sides of the diaphragm. An upstream seat is provided in the upstream chamber and opposing the upstream seal around the orifice. Below a minimum or popping pressure, the upstream seat and upstream seal coact to form a flow restricting seal to prevent CSF flow through the orifice.

In operation, differential pressures between the upstream chamber and the downstream chamber and above the popping pressure will bend or flex the diaphragm, pushing its downstream annular seal toward an opposing seat in the downstream chamber. As greater pressure is exerted against the diaphragm, the passage through which CSF flows between the annular seal and the seat in the downstream chamber becomes progressively smaller. Because of the increase in the differential pressure, however, the velocity of the fluid at the passage will increase so that the CSF flow rate remains substantially constant over a range of pressures between the aforementioned popping pressure and a second threshold pressure at which the diaphragm presses its downstream seal against the downstream seat, forming a flow-restricting seal and preventing substantial CSF flow through the outflow port in the downstream chamber. The annular downstream seal and/or the downstream seat preferably include means to allow a slight leakage of CSF, permitting slight drainage of the contact areas between the downstream seal and the downstream seat and preventing proteins in the CSF from being trapped and interfering with the proper operation of the device. A feed pipe in the downstream chamber is provided to direct CSF flow through the orifice directly to the second pressure regulation valve when the differential pressure exceeds the aforementioned second threshold value.

The aforementioned arrangement of parts provides a simple and compact device and allows the threshold or popping pressure of the first pressure regulation valve and the closing or blow-out pressure of the flow regulation valve to be adjusted independently of each other. For example, at least one of the annular seats is formed in a screw threadedly received within a wall of the housing, allowing the screw be to be positioned axially within the housing to a predetermined extent. By adjusting the screws, the positions of the upstream and downstream annular seats can be varied to set the opening pressure at a first threshold value and the closing pressure at a second threshold value. The second pressure regulation valve may be provided as a slit valve disposed in an opening passing axially through the downstream seat which forms the opening through the downstream screw.

In another embodiment of the invention, the drainage device is provided with a housing having a cylindrical chamber therein in which a ball valve is positioned to move between first and second conical end seats. The inlet duct to the first pressure regulation valve opens out in the center of the first conical seat and the outlet duct from the flow regulation valve opens out at the center of the second conical seat. A calibration spring biases the ball in the direction of the first conical seat to prevent CSF flow through the chamber when the differential pressure across the device is below the popping pressure. Under increasing pressures, the ball valve will move toward the second conical end seat. A feed duct to a second pressure regulation valve opens out from the cylindrical chamber with the second pressure regulating valve positioned outside housing to direct CSF flow to a drainage location when the differential pressure exceeds a second threshold value.

DETAILED DESCRIPTION OF THE PREFERRED EMBODIMENTS

The present invention provides a valve apparatus useful in the treatment of hydrocephalus. The apparatus of the invention includes the desirable operating characteristics of a three stage valve, regulating fluid drainage under distinct pressure and flow conditions. The invention is provided in a device which combines two pressure regulation valves and a flow regulation valve. A first pressure regulating valve is set to open at a predetermined differential pressure, or popping pressure, and is constructed in parallel with an assembly of the other valves wherein the flow regulating valve is combined in series with a second pressure regulating valve. The combination of valves operates so that, when the first pressure regulating valve is open, the flow regulating valve maintains a constant CSF flow rate through the device within a predetermined range of pressures. At a predetermined maximum differential pressure, the flow regulating valve closes and a second pressure regulating valve will open to allow drainage of CSF at higher flow rates while maintaining a substantially constant second predetermined pressure differential across the device.

Figure 1:
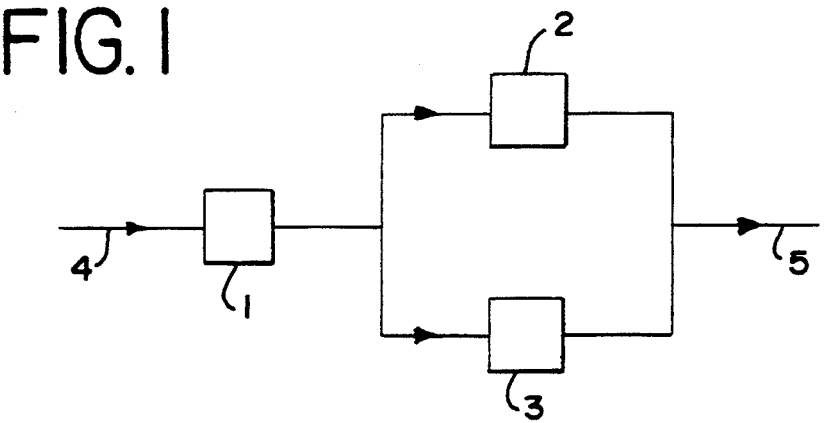
FIG. 1 is a block diagram of a drainage device according to the invention.

Referring to the various Figures, FIG. 1 schematically illustrates a preferred configuration for an apparatus of the invention. A first pressure regulation valve 1 is connected in series with an assembly having a flow regulation valve 2 in parallel with a second pressure regulation valve 3. The first valve 1 is located upstream of the assembly 2, 3. In this arrangement, when the apparatus has been surgically implanted, the upstream catheter 4 conveying CSF to the inlet of the valve 1 has its free end within a ventricle of the brain. The downstream catheter 5, connecting the outlets from the valves 2 and 3, has its free end in the drainage area of the body, such as the peritoneal region, for example.

Figure 2:
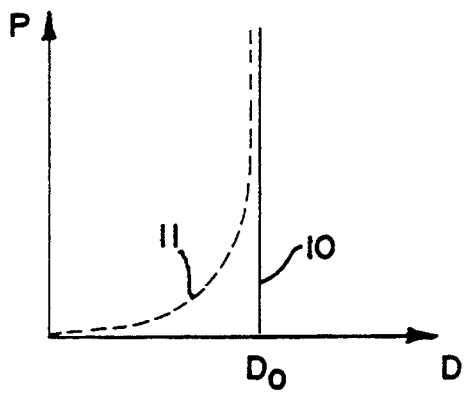
FIG. 2 is a characteristic pressure/flow curve for a flow regulation valve.
Figure 3:
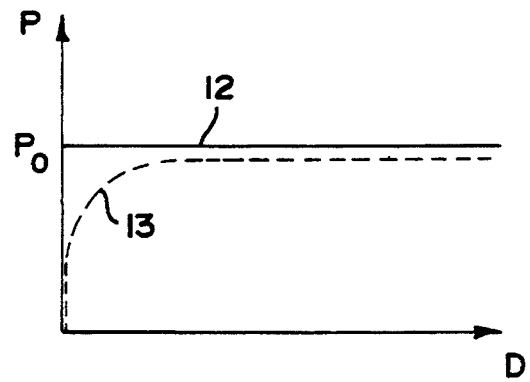
FIG. 3 is a characteristic pressure/flow curve for a pressure regulation valve.

Regarding the operation of the individual valves 1, 2 and 3, the curve of FIG. 2 illustrates a characteristic pressure/flow relationship for a flow regulation valve such as the valve 2. As shown by line 10, the valve 2 will ideally allow a fluid flow rate equal to $D_0$ to pass therethrough regardless of the differential pressure between its upstream and downstream portions. In practice, the pressure/flow curve will deviate slightly from the ideal curve 10 and typically will show a trend similar to that shown by curve 11, in a broken line. FIG. 3 shows the characteristic pressure/flow curve for a pressure regulating valve such as valve 1 or 3. Ideally, the pressure/flowrate relationship is as shown by the solid curve 12, for which the differential pressure between the upstream and downstream is constant and equal to $P_0$ whatever the flow. In practice, a curve such as curve 13 (in a broken line) is usually obtained.

Figure 4:
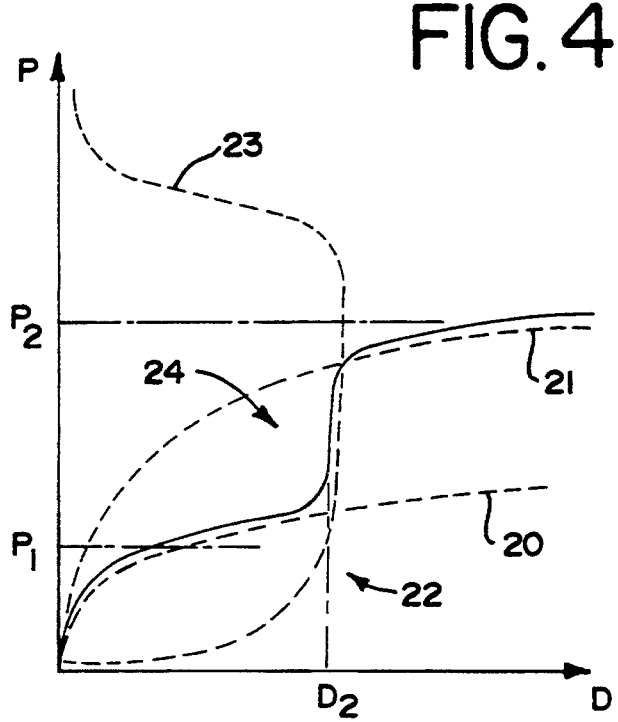
FIG. 4 is the characteristic pressure/flow curve for a drainage device according to the invention.

The characteristic pressure/flow curves for valves 1, 2 and 3 are shown again in FIG. 4 for each of the individual valves as well as for an apparatus combining the valves in accordance with the invention. For example, the characteristic curve of the pressure regulating valve 1 is shown at 20. The characteristic curve of an assembly including the pressure regulation valves 1 and 3 is shown at 21 and the characteristic curve of the flow regulation valve 2 is shown at 22. It will be understood by those in the art that the characteristic curve of the second pressure regulating valve 3 is the difference between curves 21 and 20. Unlike the curve 11 of FIG. 2, the curve 22 for flow regulating valve 2 includes a closing region 23 for a pressure equal to or greater than $P_2$, corresponding substantially to the regulation pressure of the set of valves 1 and 3. The characteristic curve of an assembly including all three valves 1, 2 and 3 is shown at 24 in a solid line.

In operation, the drainage device of the invention will prevent CSF drainage from a ventricle of the brain while the fluid pressure is below a first predetermined threshold value. When the ventricular pressure is below that threshold, the differential pressure between the ventricle and the drainage area is the same as the differential pressure within the device. When the differential pressure reaches the predetermined threshold value or popping pressure, $P_1$, the pressure regulation valve 1 opens to drain CSF from the brain and maintaining the differential pressure across the device substantially at $P_1$ within a range of flow rates. The differential pressure remains stabilized until the flow reaches the value $D_2$, imposed by the flow regulation valve 2. The flow through the valve 2 remains substantially constant over a pressure range between about $P_1$ and about $P_2$ (FIG. 4). The maximum pressure tolerated by the device is limited to $P_2$ by the closing pressure of flow regulation valve 2 and the preset opening pressure of pressure regulation valve 3. Consequently the device makes it possible to obtain a substantially constant CSF flow rate over a range of pressures regardless of the position of the patient.

Figure 5:
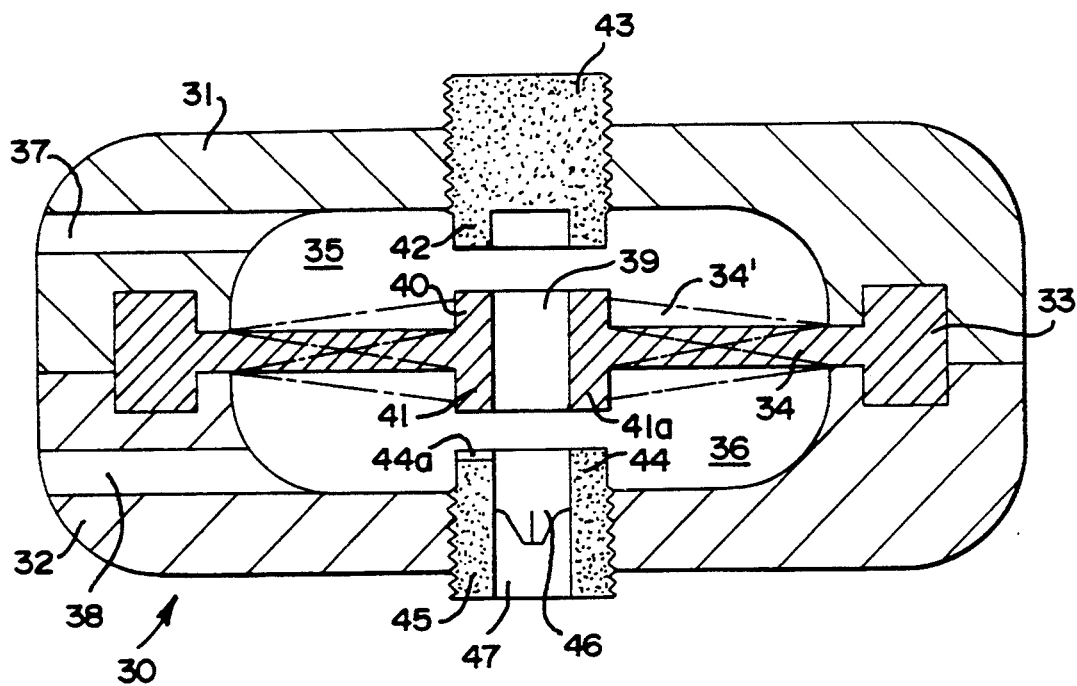
FIG. 5 is a side elevational view, in section, of a drainage device of the invention.

Referring to FIG. 5, an apparatus according to a first preferred embodiment of the invention is shown. The valve includes a housing 30 produced from a biocompatible material and having a dish shaped top 31 and a complementary bottom part 32, welded or otherwise affixed together along their peripheral edges and forming an internal cavity. The top and bottom halves 31 and 32 are provided with opposing grooves to hold the peripheral collar 33 of a flexible diaphragm 34 therein, separating the internal cavity within the housing 30 into an upstream chamber 35 and a downstream chamber 36. An inflow duct 37 passes through the upper part 31 of the housing 30 and is connected by any suitable means to the catheter 4 (FIG. 1) to form an inlet to the upstream chamber 35 of the device. An outflow duct 38 in the lower part 32 of the housing 30 constitutes one of the CSF outlets from the device. The outflow duct 38 is connected to the catheter 5 which directs excess CSF fluid to a suitable drainage area in the body.

A flow orifice 39 is provided through the center of the diaphragm 34, connecting the upstream and downstream chambers 35 and 36, the orifice 39 being bounded on the upstream side by upstream annular seal 40 and on the downstream chamber 36 side by a downstream seal 41. The seals 40 and 41 are produced in a single piece with the diaphragm 34, each seal projecting outwardly from opposing sides of the diaphragm and forming the flow orifice 39.

An annular seat 42 is provided in the upstream chamber 35 at the inner axial end of an adjustable screw 43, positioned in the top wall of the upper part 31 of the casing and coaxially aligned with the orifice 39. The seat 42 is positioned and dimensioned to interact with the upstream seal 40 of the diaphragm 34. Similarly, a downstream seat 44 is provided in downstream chamber 36 at the inner axial end of a screw 45 positioned in the bottom wall of the lower part 32 of the casing and coaxially aligned with the orifice 39 and the screw 43, so that the seat 44 can interact with the downstream seal 41 of the diaphragm. The surface of the downstream seat 44 is preferably provided with radial grooves 44a allowing a slight leakage when the downstream seal 41 is pressed on the seat 44. Alternately, the sealing surface 41a of the seal 41 could have a tapered shape, widening out in the direction of the seat 44 so as to form a flexible lip to also allow a slight leakage. A slit (or "duck-bill") valve 46 is located in a duct 47 in the downstream screw 45. The slit valve 46 corresponds to the second pressure regulating valve 3 of FIG. 1.

Below the preset popping pressure, $P_1$, the diaphragm 34, for example a bellows diaphragm, is at rest in its position shown in broken lines 34', with the upstream seal 40 bearing against the upstream seat 42. In this arrangement, all flow of CSF from the brain is blocked. When the differential pressure on each side of the diaphragm 34 exceeds the preset threshold, $P_1$, the seal 40 moves away from the seat 42, allowing CSF to flow from upstream chamber 35 through the orifice 39 and into the downstream chamber 36. In this arrangement the diaphragm 34 and the seat 42 behave like the pressure regulation valve 1 of FIG. 1.

As the differential pressure increases, the diaphragm will deform to a greater extent, moving the downstream seal 41 closer to the downstream seat 44. The higher the differential pressure, the closer the seal 41 approaches the seat 44, increasingly restricting the flow of CSF to the outflow duct 38 as the pressure increases. The assembly of the diaphragm 34 and the downstream seat 44 consequently behave like the flow regulation valve 2.

When the differential pressure reaches a certain second predetermined threshold, $P_2$, the downstream seal 41 is pressed against the downstream seat 44, forming a flow restricting seal and thereby isolating the upstream and downstream chambers 35 and 36. The slit valve 46 will then, open, disposing of CSF fluid through the outlet of the duct 47 which is connected by any suitable means to the catheter 5. The slit valve 46 will allow CSF to be drained at higher flow rates while maintaining a substantially constant differential pressure, $P_2$, across the valve.

Figure 6:
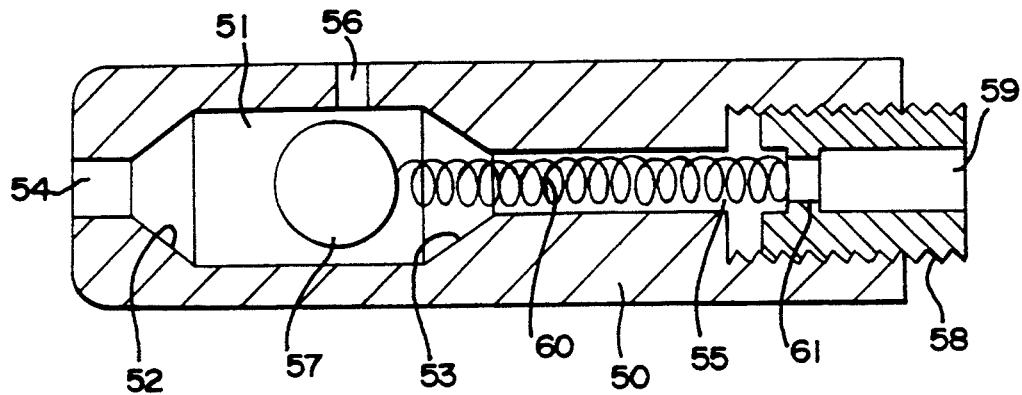
FIG. 6 is a side elevational view, in axial section, of a second drainage device according to a second embodiment of the invention.

Referring now to FIG. 6, a second preferred embodiment of the invention is shown as a valve including a housing 50, forming a cylindrical cavity 51 which is terminated at its two ends by the upstream and downstream tapered seats 52 and 53, respectively. An inflow duct 54 leads into the tapered upstream seat 52 and outflow duct 55 opens out from the tapered seat 53. An orifice 56 is drilled in the wall of the casing 53 to allow CSF communication between the cavity 51 and a second pressure regulation valve such as valve 3 in FIG. 1. A ball valve 57 is positioned in the cavity 51 to move between the tapered seats 52 and 53. An adjustment screw 58 is threadably positioned within the casing 50 and aligned coaxially with the cavity 51 and the ducts 54 and 55. The screw 58 includes an axial duct 59, connecting the outflow duct 55 to the outside of the casing and to the catheter 5, leading to the drainage location. A spring 60 in the outflow duct 55 bears against the ball valve 57 and against a shoulder 61 formed at the upstream end of the duct 59 in the adjustment screw 58. The spring 60 biases the ball 57 towards the upstream tapered seat 52 with a force which can be adjusted by adjusting the screw 58. The orifice 56 is connected to the inlet of a pressure regulation valve of a known type.

The device of FIG. 6 is implanted with the duct 54 connected to the downstream end of the catheter 4 and the duct 59 connected to the upstream end of the catheter 5, which is also connected the outlet of the aforesaid second pressure regulation valve in the orifice 56. In the absence of any differential pressure between the ducts 54 and 59, the ball valve 57 remains biased within the upstream seat 52, closing the valve under the applied force of the spring 60 pushing the ball 57. When the differential pressure reaches a certain first predetermined threshold, $P_1$, the ball 57 is pushed away from the tapered seat 52 and consequently behaves like the pressure regulation valve 1, maintaining a substantially constant differential pressure across the valve.

When the differential pressure increases, the CSF flow rate increases and the ball 57 is moved towards the tapered downstream seat 53 until it is close to the latter, where is behaves like the flow regulation valve 2, maintaining a substantially constant flow rate over a range of pressures. At a second predetermined maximum differential pressure threshold, $P_2$, the ball 57 is pressed against the tapered seat 53, closing the outflow duct 55. The pressure regulation valve connected to the bore hole orifice 56 and the upstream end of the catheter 5 has its threshold pressure adjusted to correspond to the second predetermined pressure differential, $P_2$, behaving like the pressure regulation valve 3 and allowing CSF drainage at higher flow rates. The device of FIG. 6, associated with a suitably calibrated pressure regulation valve to regulate flow through orifice 56, makes it possible to obtain the characteristic pressure/flow curve of FIG. 4.

While a detailed description of the preferred embodiments has been set forth, those skilled in the art will appreciate that various changes and modifications to those embodiments are possible and are within the scope of the invention, as defined by the following claims.

I claim:

1. A surgically implantable drainage device for the treatment of hydrocephalus, comprising:
    a first pressure regulating valve having first opening means to allow fluid to flow therethrough at a first predetermined pressure;
    a flow regulation valve to regulate the flow of fluid through the drainage device when said first pressure regulating valve is in an opened condition, said flow regulation valve providing a substantially constant flow rate over a range of pressures from said first predetermined pressure to a second predetermined pressure;
    a second pressure regulating valve having second opening means to allow fluid from said first pressure regulating valve to pass therethrough, said second opening means being responsive to fluid pressure exerted thereon to open said second pressure regulating valve at said second predetermined pressure, said second predetermined pressure being greater than said first predetermined pressure; and
    said first pressure regulating valve arranged in series with both said flow regulation valve and said second pressure regulating valve, said flow regulating valve arranged in parallel with said second pressure regulating valve.

2. The drainage device of claim 1 wherein said first pressure regulating valve, said flow regulation valve, and said second pressure regulating valve are combined within a housing having a fluid inflow duct and a fluid outflow duct, said first pressure regulating valve and said flow regulation valve including a flexible diaphragm dividing said housing into an upstream chamber associated with said inflow duct and a downstream chamber associated with said outflow duct, said diaphragm having an orifice extending therethrough to permit fluid communication between said upstream side thereof, said first downstream chamber, said diaphragm including a first annular seal surrounding said orifice on the upstream side thereof, said first pressure regulation valve including a first circular seat positioned in said upstream chamber and adapted to form a flow-restricting seal with said first annular seal to substantially prevent fluid from flowing from said upstream chamber and into said downstream chamber when the pressure differential between said upstream and downstream chambers is less than said first predetermined pressure.

3. The drainage device of claim 2 wherein said diaphragm further includes a second annular seal surrounding said orifice on the downstream side thereof, said flow regulation valve and said second pressure regulating valve further including a second circular seat in said downstream chamber and adapted to form a flow-restricting seal with said second annular seal on said diaphragm to substantially prevent fluid from exiting said downstream chamber through said outflow duct when the pressure differential between said upstream and downstream chambers reaches a second predetermined pressure greater than said first predetermined pressure.

4. The drainage device of claim 3 wherein said second annular seal and said second circular seat include leakage means to allow fluid leakage through said flow-restricting seal.

5. The drainage device of claim 4 wherein said second circular seat forms the flow inlet to said second pressure regulating valve, said second pressure regulating valve opening when said second annular seal and said second circular seat form said flow restricting seal to direct the flow of fluid through said flow inlet and through said second pressure regulating valve.

6. The drainage device of claim 1 wherein said first pressure regulating valve and said flow regulation valve are housed within a cylindrical chamber having a pair of tapered end seats therein and a ball valve configured to move between said end seats, an inlet flow duct is associated with a first end seat and an outlet flow duct is associated with a second end seat, said ball valve associated with biasing means to bias said ball valve in said first end seat to prevent the flow of fluid through said inlet flow duct when the pressure differential across the device is below said first predetermined pressure, said biasing means allowing said ball valve to move away from said first end seat to allow fluid to flow through said chamber in response to a pressure differential greater than said first predetermined pressure, said ball valve closing said fluid outflow duct at said second predetermined pressure.

7. The drainage device of claim 6 wherein said second pressure regulating valve is positioned externally of said chamber, said housing having a bore hole therethrough for fluid communication between said chamber and said second pressure regulating valve.

8. A surgically implantable drainage device for regulating the passage of cerebrospinal fluid from a source location in the brain to a drainage location in the body, the drainage device comprising:
- a biocompatible housing;
- a flexible diaphragm mounted within said housing and dividing the interior thereof into an upstream chamber and a downstream chamber, said diaphragm including a central orifice to allow cerebrospinal fluid communication between said upstream and said downstream chambers;
- said diaphragm having an upstream valve seal thereon surrounding said orifice on the upstream side thereof and a downstream valve seal surrounding said orifice on the downstream side thereof, said upstream and said downstream valve seals defining a passageway from said upstream chamber to said downstream chamber;
- an inflow port for communicating cerebrospinal fluid from the source location to said upstream chamber;
- an outflow port for communicating cerebrospinal fluid from said downstream chamber to a drainage location;
- an upstream valve seat in said upstream chamber adapted to form a flow-restricting seal with said upstream valve seal on said diaphragm when the pressure differential between said upstream and said downstream chambers is below a first predetermined pressure, thereby preventing cerebrospinal fluid communication between said upstream and said downstream chambers;
- downstream sealing means for forming a flow-restricting seal with said downstream valve seal on said diaphragm when the pressure differential between said upstream and said downstream chambers exceeds a second predetermined pressure, thereby preventing substantial cerebrospinal fluid communication between said orifice and said orifice and said outflow port; and
- a pressure regulating valve in operative association with said downstream sealing means for allowing cerebrospinal fluid communication between said upstream chamber and the drainage location when said pressure differential exceeds said second predetermined pressure, said pressure regulating valve maintaining a substantially constant pressure differential between said upstream and said downstream chambers.

9. The drainage device of claim 8 wherein said upstream valve seat forms the end of an adjustable screw having a shank portion threadedly received in an aperture in said housing, said screw being adjustable within said aperture to thereby set said first predetermined threshold.

10. The drainage device of claim 8 wherein said downstream sealing means includes a downstream valve seat, said downstream seat forming the flow inlet to said pressure regulating valve, said pressure regulating valve being set to open at said second predetermined threshold when said downstream seat and said downstream valve seal form said flow restricting seal therebetween.

11. The drainage device of claim 10 wherein said downstream sealing means and aid downstream valve seat include leakage means to allow a cerebrospinal fluid leakage through said flow-restricting seal.

12. A surgically implantable drainage device for regulating the passage of cerebrospinal fluid from a source location in the brain to a drainage location in the body, the drainage device comprising:
- a biocompatible housing having a fluid flow chamber therein;
- a first seat at an upstream end of said chamber and a second seat at a downstream end of said chamber;
- an inflow port for communicating cerebrospinal fluid from the source location to said first seat;
- an outflow port for communicating cerebrospinal fluid from said second seat to the drainage location;
- a movable valve member positioned within said chamber and configured to move between said first and said second seats;
- biasing means in operative association with said movable valve member to hold said valve member in said first seat and forming a flow restricting seal therein to substantially prevent cerebrospinal communication between said inflow port and said chamber when the fluid pressure differential between the source location and the drainage location is below a first predetermined threshold;
- said biasing means constructed to respond to changes in said pressure differential to move said movable valve member from a position within said first seat to a position within said second seat as said pressure differential increases, permitting cerebrospinal fluid communication between said inflow port and said outflow port when said pressure differential exceeds said first predetermined threshold, said biasing means moving said movable valve member away from said first seat when said pressure differential exceeds said first threshold, forming a flow-restricting seal between said movable valve member and said second seat to substantially prevent cerebrospinal fluid communication between said chamber and said outflow port when said pressure differential exceeds a second predetermined threshold, said biasing means and said movable valve member maintaining a substantially constant cerebrospinal fluid flow rate through said chamber when the pressure differential is between said first predetermined threshold and said second predetermined threshold;
- a pressure regulating valve associated with said biasing means and said movable valve member for regulating the flow of cerebrospinal fluid when said pressure differential exceeds said second predetermined threshold, said pressure regulating valve communicating said cerebrospinal fluid between said inflow port and said drainage location while maintaining a substantially constant pressure differential between said source location and said drainage location.

13. The drainage device of claim 12 wherein said first and second seats are conical in configuration, having their widest ends opening into said chamber.

14. The drainage device of claim 12 wherein said biasing means further includes an adjustment screw and a spring associated therewith, said adjustment screw being threadedly received within said housing and aligned coaxially with said outflow port, said screw including a shoulder dimensioned to bear against one end of said spring, said spring positioned within said outflow port and having its other end associated with said movable valve member, said spring biasing said movable valve member toward said first seat and said adjustment screw allowing the adjustment of said first predetermined value.

15. The drainage device of claim 12 wherein said pressure regulating valve is positioned outside of said biocompatible housing and in operative association with said fluid flow chamber, said fluid flow chamber including a fluid flow passageway to communicate cerebrospinal fluid between said chamber and said pressure regulating valve when the pressure differential across the device exceeds said second predetermined threshold.

* * * * *